(12) United States Patent
Salehi-Abari et al.

(10) Patent No.: US 11,842,245 B2
(45) Date of Patent: Dec. 12, 2023

(54) AUTOMATED SOIL MOISTURE EFFECTS SENSOR WITH IMPROVED RFID SYSTEM

(71) Applicants: Omid Salehi-Abari, Waterloo (CA); Srinivasan Keshav, Cambridge (GB); Ju Wang, Montreal (CA)

(72) Inventors: Omid Salehi-Abari, Waterloo (CA); Srinivasan Keshav, Cambridge (GB); Ju Wang, Montreal (CA)

(*) Notice: Subject to any disclaimer, the term of this patent is extended or adjusted under 35 U.S.C. 154(b) by 376 days.

(21) Appl. No.: 17/200,535

(22) Filed: Mar. 12, 2021

(65) Prior Publication Data

US 2021/0286961 A1 Sep. 16, 2021

Related U.S. Application Data

(60) Provisional application No. 62/989,439, filed on Mar. 13, 2020.

(51) Int. Cl.
| | |
|---|---|
| *G01L 9/00* | (2006.01) |
| *G06K 7/10* | (2006.01) |
| *G05B 19/4155* | (2006.01) |
| *A01G 27/00* | (2006.01) |
| *A01G 25/16* | (2006.01) |

(52) U.S. Cl.
CPC ....... *G06K 7/10366* (2013.01); *A01G 27/003* (2013.01); *G05B 19/4155* (2013.01); *A01G 25/167* (2013.01); *G05B 2219/40269* (2013.01)

(58) Field of Classification Search
None
See application file for complete search history.

(56) References Cited

U.S. PATENT DOCUMENTS 9,554,509 B2 * 1/2017 Bischoff ............... A01D 41/127
9,756,774 B1 * 9/2017 Wilson ................. A01B 79/005

OTHER PUBLICATIONS

Aroca R., Hernandes A., Magalhaes D., Becker M., Vaz C., and Calbo A., Application of Standard EPC/GEN2 UHF RFID Tags as Soil Moisture Sensors, Multidisciplinary Digital Publishing Institute Proceedings, vol. 1 (Nov. 14, 2016).

(Continued)

*Primary Examiner* — Brandi N Hopkins
*Assistant Examiner* — Nigel H Plumb
(74) *Attorney, Agent, or Firm* — Brill Law Office; Jeffrey Brill

(57) ABSTRACT

A novel method and system is disclosed for using a commodity RFID system for automatically measuring levels of soil moisture in planting containers. A large number of planting containers are used to grow pots in soil in a greenhouse. An RFID reader interrogates passive RFID tags affixed to the planting containers. The RFID reader can be attached to a robotic arm configured to move above multiple rows and columns of containers. Signal features of specific passive RFID tags affixed to specific ones of the containers are automatically monitored, including a minimum response threshold of RFID reader transmission power to activate the passive RFID tag ("MRT"), based on the wireless interrogation of specific tags by the reader. Soil moisture levels of specific containers are then automatically determined based on the signal features of the attached tags, and effects of soilure moisture on electromagnetic fields of antennas of tags.

19 Claims, 7 Drawing Sheets

(56) References Cited

OTHER PUBLICATIONS

Aroca R., Hernandes A., Magalhaes D., Becker M., Vaz C., and Calbo A., Calibration of Passive UHF RFID Tags Using Neural Networks to Measure Soil Moisture, Journal of Sensors, vol. 2018, Article ID 3436503 (May 22, 2018).

Ding and Chandra. Estimating Soil Moisture and Electrical Conductivity Using Wi-Fi, Proceedings of ACM MobiCom (2019).

Hasan, Bhattacharyya, and Sarma, Towards Pervasive Soil Moisture Sensing Using RFID Tag Antenna-Based Sensors, 2015 Institute for Electrical and Electronics Engineers ("IEEE") Conference on RFID Technology and Applications (RFID-TA), pp. 165-170.

S. Kim, T. Le, M. M. Tentzeris, A. Harrabi, A. Collado, and A. Georgiadis. An RFID-enabled Inkjet-printed Soil Moisture Sensor on Paper for "Smart" Agricultural Applications, Institute for Electrical and Electronics Engineers ("IEEE") Sensors, pp. 1507-1510 (2014).

Kruk, and J. A. Huisman. Measuring Soil Water Content with Ground Penetrating Radar: a Decade of Progress, Vadose Zone Journal, 17(1) (2018).

E. Lichtenberg, J. Majsztrik, and M. Saavoss, Profitability of Sensor-based Irrigation in Greenhouse and Nursery Crops, HortTechnology, 23(6), pp. 770-774 (2013).

B. P. Mohanty, M. H. Cosh, V. Lakshmi, and C. Montzka, Soil Moisture Remote Sensing: State-of-the-Science, Vadose Zone Journal, 16(1) (2017).

K. Noborio. Measurement Of Soil Water Content and Electrical Conductivity by Time Domain Reflectometry: a Review, Computers and Electronics in Agriculture, 31(3). pp. 213-237 (2001).

S. Pichorim, N. Gomes, and J. Batchelor, Two Solutions Of Soil Moisture Sensing with RFID for Landslide Monitoring, Sensors, 18(2):452 (2018).

L. Ruiz-Garcia and L. Lunadei, The Role of RFID in Agriculture: Applications, Limitations and Challenges, Computers and Electronics in Agriculture, 79(1), pp. 42-50 (2011).

Tagformance Pro Brochure, [online] Voyantic Ltd., 2019, [retrieved on Sep. 18, 2023]. Retrieved from the Internet <URL: https://voyantic.com/resources/#catalogues>.

J. Wang, O. Abari, S. Keshav, Challenge: RFID Hacking for Fun and Profit, Proceedings of 24th Annual International Conference on Mobile Computing and Networking, New Delhi, India, Oct. 29-Nov. 2, 2018 (MobiCom'18), pp. 1-10.

J. Wang and B. Choudhury, Remote Sensing of Soil Moisture Content Over Bare Field at 1.4 GHZ Frequency, Journal of Geophysical Research: Oceans, 86(C6):5277-5282 (1981).

* cited by examiner

AUTOMATED SOIL MOISTURE EFFECTS SENSOR WITH IMPROVED RFID SYSTEM

CROSS-REFERENCE TO RELATED APPLICATIONS

The present application claims the benefit under 35 U.S.C. § 119(e) of U.S. Provisional Patent Application Ser. No. 62/989,439, entitled "Soil Moisture Sensing with Commodity RFID Systems," filed on Mar. 13, 2020, the entire contents of which are incorporated herein by reference.

TECHNICAL FIELD

The present disclosure generally relates to technology for determining soil moisture levels, and more specifically to sensing and measuring soil moisture using commodity RFID systems.

BACKGROUND

A greenhouse provides a highly controlled, pest-free environment for growing plants. Greenhouses provide optimum growing environments for plants despite adverse climatic conditions, making them especially important in an era of changing climate. There are estimated to be more than 9 million greenhouses worldwide, and it is reported that their market value will increase to about 1.3 billion USD in 2022. Thus, improving the productivity of greenhouses has the potential for significant real-world impact.

A typical commercial greenhouse hosts between a thousand and a million plants that are grown in pots that contain soil. Many pots are deployed on trays with a separation of few decimeters. To prevent damage to leaves, plants are watered by filling trays with water and letting the plants absorb water from the trays.

Measuring soil moisture levels in these pots frequently (e.g., daily) is very important. Maintaining suitable moisture levels is critical for the health of the plants. Low soil moisture can cause plants to grow slowly or even die; excessive moisture can cause fungal diseases that harm or kill plants. In addition, maintaining proper moisture levels saves up to 25% of irrigation water. Conventionally, to maintain a proper soil moisture level, greenhouse staff manually check the moisture level of all pots every day, using their bare fingers as probes. When the soil moisture level is below a threshold, watering pipe add water into the trays.

Some dedicated soil moisture sensors do exist, but these conventional sensors are too expensive to practicably deploy in in each pot of a commercial greenhouse to monitor its soil moisture level. For example, an ECHO-EC5 soil moisture sensor currently costs $169, in addition to the need for an Arduino controller that costs around $35 USD. Watermark moisture sensors and electromagnetic soil moisture sensors are used for irrigation scheduling. MEMS moisture sensors and SHT15 humidity sensors are used for monitoring the moisture of concrete structures. To reveal the fine-grained, dynamic moisture changes in an outdoor landscape, a reactive soil moisture sensor network is designed by Cardell et al. Although these conventional sensors can measure soil moisture, they are too expensive to practicably deploy at each pot in a commercial greenhouse.

It would be desirable to address these issues.

SUMMARY

A commodity RFID system is used for automatically measuring levels of soil moisture in planting containers. A large number of planting containers are used to grow pots in soil, for example in a greenhouse. One or more RFID readers are used to interrogate passive RFID tags affixed to or inside of the multiple planting containers. In some implementations Type-E passive RFID tags are used, but other types of off-the-shelf passive RFID tags can be used in other implementations. The RFID reader can be attached to a robotic arm that is configured to move above multiple rows and columns of containers within signal range, such that the reader communicates with the tags affixed to the containers as the robotic arm moves. Signal features of specific passive RFID tags affixed to specific ones of the containers are automatically monitored, based on the wireless interrogation of the specific tags by the reader. Soil moisture levels of specific containers are then automatically determined based on the signal features of the attached RFID tags, and effects of soilure moisture on electromagnetic fields of antennas of passive RFID tags. When an RFID tag is attached to a pot containing soil, there is a coupling effect between the tag's antenna and the soil, since the tag is physically proximate to the soil. The coupling changes the electromagnetic field of the tag's antenna, resulting in changes to the channel over the tag's antenna. The amount of coupling is affected by the soil moisture level. Thus, when soil moisture varies, the channel over a tag's antenna will also change, causing changes to the signal feature readings at the RFID reader. Based on this, changes in the soil moisture level of specific containers can be automatically detected based on changes in the signal features of associated RFID tags.

In some implementations, the signal feature utilized for soil moisture sensing is the minimum response threshold of RFID reader transmission power to activate a passive RFID tag ("MRT"). In another implementation, received signal strength ("RSS") of the reflection signal of a passive RFID tag is used, although MRT is less subject to variance resulting from an environment with RF noise. This is because MRT is based on a one way transmission between the reader and the tag, whereas RSS as based on a round trip transmission. Where MRT is used, a low pass filter may be applied to raw MRT readings $\{x_1, \ldots x_i \ldots x_N\}$ taken for a specific passive RFID tag. For example, a filtered MRT value $y_i$ can be calculated as $y_i = \alpha \cdot x_i + (1-\alpha) \cdot y_{i-1}$, $2 \leq i \leq N$, where $y_1 = x_1$ and $\alpha =$ a given smoothing factor. The filtered MRT values may then be used to automatically determine soil moisture levels.

Because MRT is still subject to variance based on changes in the location of the container (and hence the affixed RFID tag), in some implementations differential MRT ("DMRT") is used for soil moisture sensing. More specifically, two passive RFID tags are proximately positioned to each container. A first (sensing) tag is positioned below the level of soil in a container, and a second (reference) tag is positioned above the level of soil. For example, the sensing tag can be affixed to the outside of the given container below the level of soil, and the reference RFID tag may be affixed to the outside of the given container above the level of soil. The coupling between the reference tag and the soil is not strong enough to affect the MRT because the tag is above the soil level, whereas the sensing tag positioned below the soil level strongly couples to the soil and its MRT is affected. The DMRT can then be calculated as the difference between the MRT of the sensing tag and the MRT of the reference tag. Because both MRTs are equally affected by the position of the container but only the sensing tag's MRT is affected by the soil moisture level, the DMRT is robust against variations caused by changes to container location. The DMRT can then be used to automatically determine the soil moisture level of the given container.

To calibrate the system, features of signals can be automatically mapped to soil moisture levels by measuring signal feature values $[x_1, \ldots, x_i, \ldots, x_I]$ at specific discrete soil moisture levels $[M_1, \ldots, M_i, \ldots, M_I]$ ranging from 0% to 100%. A polynomial equation $M_i = p_1 x_i^n + p_2 x_i^{n-1} + \ldots + p_n x_i + p_{n+1}$ can then be used to map the signal feature values $[x_1, \ldots, x_i, \ldots, x_I]$ to the specific discrete soil moisture levels $[M_1, \ldots, M_i, \ldots, M_I]$, to determine a corresponding moisture level for a given signal feature value.

In some implementations, the containers are positioned on one or more watering trays. At least one watering pipe is configured to add water to the tray(s). In responsive to determining that soil moisture levels are below a given threshold, the flow of water through the pipe(s) can be turned on automatically to irrigate containers positioned on watering tray(s).

The features and advantages described in this summary and in the following detailed description are not all-inclusive, and particularly, many additional features and advantages will be apparent to one of ordinary skill in the relevant art in view of the drawings, specification, and claims hereof.

The Figures depict various implementations for purposes of illustration only. One skilled in the art will readily recognize from the following discussion that other implementations of the subject matter illustrated herein may be employed without departing from the principles described herein.

DETAILED DESCRIPTION

As described in more detail below, commodity passive RFID tags are placed on planting containers in a greenhouse. For example, RFID tags can be affixed to the outside of or placed inside pots containing soil in which plants are grown. An RFID reader interrogates the RFID tags. A signal feature of the tags is monitored, and used to determine soil moisture levels of the containers. More specifically, the soil moisture levels are determined based on the monitored signal feature of the RFID tags, and effects of soilure moisture on electromagnetic fields of antennas of the RFID tags. A detected change in the monitored signal feature of a specific RFID tag indicates a corresponding change in the soil moisture level of the associated planting container. In some implementations, the signal feature to monitor is the minimum response threshold of RFID reader transmission power to activate the commodity passive RFID tag ("MRT"). In other implementations Received Signal Strength ("RSS") is monitored in this context, although MRT is less prone to variations due to RF noise. In some implementations, two passive RFID tags are proximately positioned to each container, the first below the soil level and the second above the soil level. In this scenario, the differential MRT ("DMRT") of the first tag and second tag is calculated as the difference between the MRT of the first tag and the MRT of the second tag. The soil moisture of the container is then calculated based on DMRT. The use of DMRT in this context provides resilience to changes in container (and hence tag) locations, as explained in more detail below. In some implementations, the RFID reader is attached a movable robotic arm which is configured to automatically move above multiple rows and columns of containers and wirelessly communicate with the RFID tags attached thereto. In response to determining that soil moisture levels are below a given threshold, planting containers may be automatically irrigated, for example by using a watering pipe to irrigate trays on which the planting container are positioned.

Figure 1:
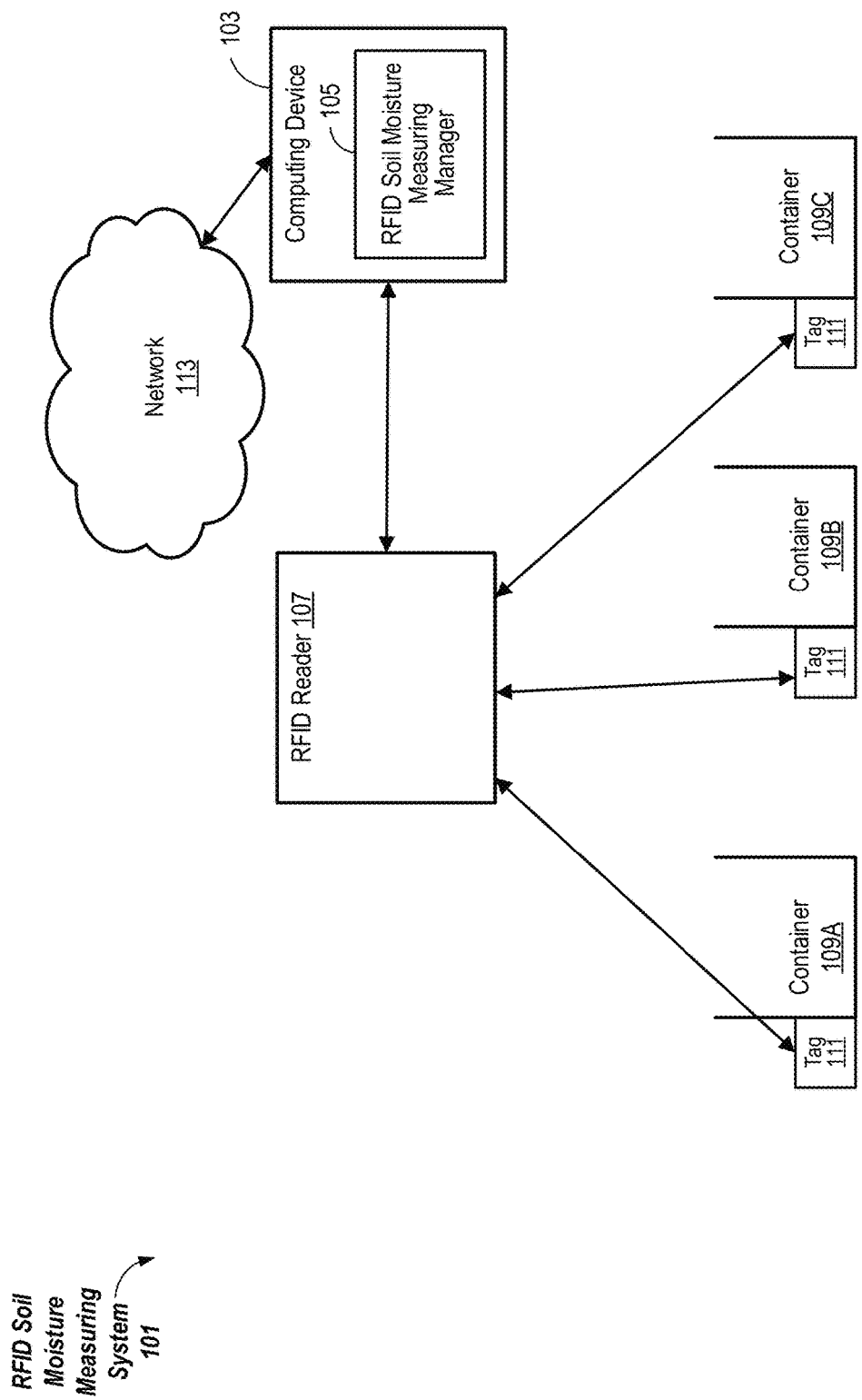
FIG. 1 is a block diagram of an exemplary configuration of an RFID soil moisture measuring system, according to some implementations.

FIG. 1 illustrates an exemplary configuration in which an RFID soil moisture measuring system 101 can operate. For example, the RFID soil moisture measuring system 101 is deployed in a greenhouse, although in other implementations an RFID soil moisture measuring system 101 can be utilized in other contexts. Multiple planting containers 109 (e.g., pots made of clay, plastic and/or other suitable substances) are present in the greenhouse. The planting containers 109 contain soil and, typically, plants growing in the soil (the soil and plants are not specifically illustrated in FIG. 1). As the term is used herein, "soil" means any suitable media for growing plants in pots and similar planting containers, including different container mixes that do and do not contain dirt, as well as vermiculite, perlite, sphagnum moss, various minerals, different types of organic matter, etc.

For the sake of illustrative clarity, FIG. 1 illustrates only three planting containers 109A-109C, but it is to be understood that in practice orders of magnitude more planting containers 109 would typically be present in a greenhouse (e.g., thousands, tens of thousands, a million, etc.). One or more RFID tags 111 are affixed to or inside of each planting container 109. In the example configuration of FIG. 1, two RFID tags 111 are affixed to the outside of each planting container 109. As discussed below in more detail, in other implementations, a single RFID tag 111 may be affixed to each container 109, and the placement of the tags on or in the containers can vary. Different types of commodity passive RFID tags 111 may be used in different implementations, as discussed in more detail below.

An RFID reader 107 is positioned above the planting containers 109, within a suitable distance for communicating with the RFID tags 111. A conventional RFID reader 107 can be used in this context. In one implementation an Impinj Speedway® R420 reader is used without any hardware or firmware modification, but this is just an example. In other implementations other RFID readers 107 may be used. In some implementations, multiple RFID readers 107 are deployed in the RFID soil moisture measuring system 101. Specific placement of the RFID reader 107 and suitable distances between the reader 107 and the tags 111 in the context of the RFID soil moisture measuring system 101 discussed in greater detail below. As illustrated and described in more detail below in conjunction with FIG. 6, in some implementations the RFID reader 107 is attached to a robotic arm that is configured to move above rows and columns of pots at a suitable distance.

An RFID soil moisture measuring manager 105 residing on a computing device 103 is illustrated in FIG. 1. As described in more detail below, the RFID soil moisture measuring manager 105 executes various functionalities as part of the operation of the RFID soil moisture measuring system 101. The illustration of the RFID soil moisture measuring manager 105 residing on a single computing device 103 is an example only, and in different implementations various ones of the functionalities described herein can be instantiated on various types of computing devices 103, or can be distributed between multiple computing devices 103 as desired.

The RFID soil moisture measuring manager 105 is communicatively coupled to the RFID reader 107, for example through an ethernet cable or other type of wired or wireless connection between the RFID reader 107 and the computing device. RFID reader protocol may be used for the communication between the RFID reader 107 and the RFID soil moisture measuring manager 105.

The computing device 103 can be implemented using computer systems 210 such as the one illustrated in FIG. 2 and described below. The computing device 103 may be communicatively coupled to a network 113 (e.g., the internet), for example via a network interface 248 as described below in conjunction with FIG. 2.

Figure 2:
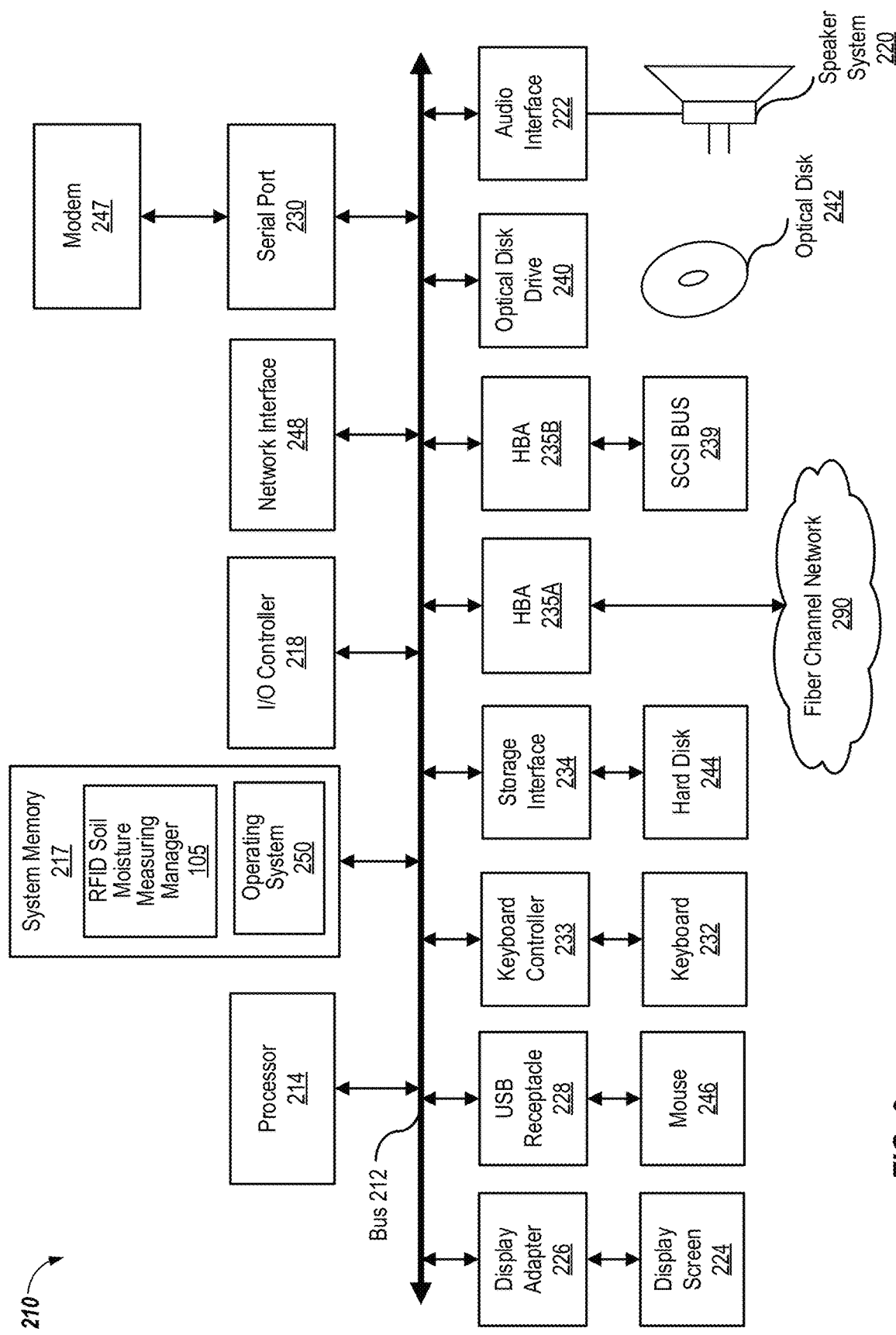
FIG. 2 is a block diagram of a computer system suitable for implementing an RFID soil moisture measuring manager, according to some implementations.

FIG. 2 is a block diagram of a computer system 210 suitable for implementing a RFID soil moisture measuring manager 105. Both endpoints 103 and servers 105 can be implemented in the form of such computer systems 210. A computer system 210 of the type illustrated in FIG. 2 can but need not be in the form of a mobile computing device. As illustrated, one component of the computer system 210 is a bus 212. The bus 212 communicatively couples other components of the computer system 210, such as at least one processor 214, system memory 217 (e.g., random access memory (RAM), read-only memory (ROM), flash memory), an input/output (I/O) controller 218, an audio output interface 222 communicatively coupled to an external audio device such as a speaker system 220, a display adapter 226 communicatively coupled to an external video output device such as a display screen 224, one or more interfaces such as serial ports 230, Universal Serial Bus (USB) receptacles 230, parallel ports (not illustrated), etc., a keyboard controller 233 communicatively coupled to a keyboard 232, a storage interface 234 communicatively coupled to at least one hard disk 244 (or other form(s) of, e.g., magnetic and/or solid state media), a host bus adapter (HBA) interface card 235A configured to connect with a Fibre Channel (FC) network 290, an HBA interface card 235B configured to connect to a SCSI bus 239, an optical disk drive 240 configured to receive an optical disk 242, a mouse 246 (or other pointing device) coupled to the bus 212 e.g., via a USB receptacle 228, a modem 247 coupled to bus 212, e.g., via a serial port 230, and a network interface 248 coupled, e.g., directly to bus 212.

Other components (not illustrated) may be connected in a similar manner (e.g., document scanners, digital cameras, printers, etc.). Conversely, all of the components illustrated in FIG. 2 need not be present. The components can be interconnected in different ways from that shown in FIG. 2.

The bus 212 allows data communication between the processor 214 and system memory 217, which, as noted above may include ROM and/or flash memory as well as RAM. The RAM is typically the main memory into which the operating system and application programs are loaded. The ROM and/or flash memory can contain, among other code, the Basic Input-Output system (BIOS) which controls certain basic hardware operations. Application programs can be stored on a local computer readable medium (e.g., hard disk 244, optical disk 242) and loaded into system memory 217 and executed by the processor 214. Application programs can also be loaded into system memory 217 from a remote location (i.e., a remotely located computer system 210), for example via the network interface 248 or modem 247. In FIG. 2, the RFID soil moisture measuring manager 105 is illustrated as residing in system memory 217. The workings of the RFID soil moisture measuring manager 105 are explained in greater detail below. An operating system 250 is also illustrated as residing in system memory 217. Different operating systems can be utilized in different implementations as desired, such as Linux, Windows, mac OS, etc.

The storage interface 234 is coupled to one or more hard disks 244 (and/or other form of storage media). The storage media may be a part of computer system 210, and/or may be physically separate and accessed through other interface systems.

The network interface 248 and or modem 247 can be directly or indirectly communicatively coupled to a network 113 such as the internet. Such coupling can be wired or wireless.

Figure 3:
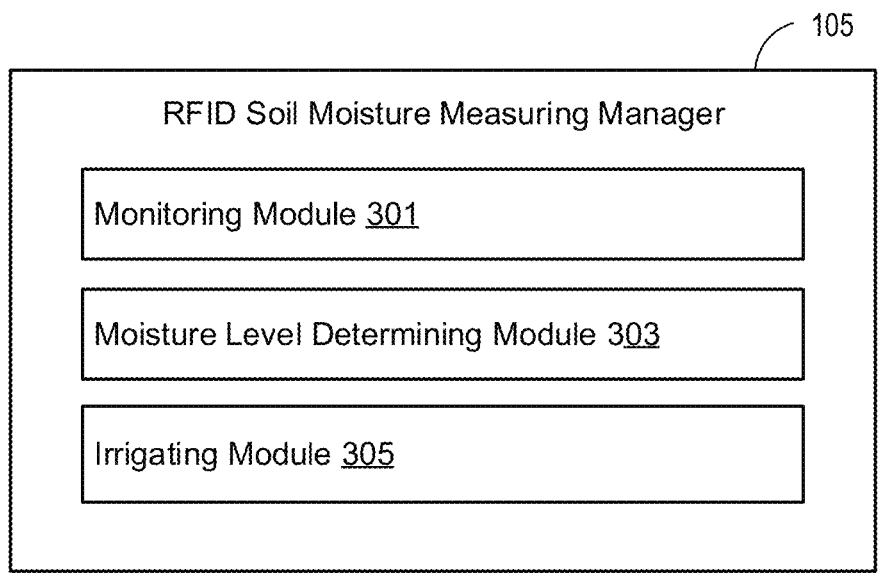
FIG. 3 is a block diagram of the modules of an RFID soil moisture measuring system, according to some implementations.
Figure 4A:
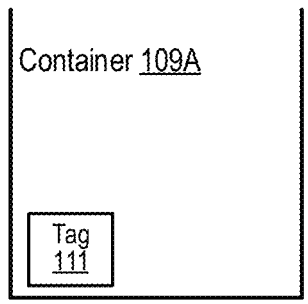
FIG. 4A-D are diagrams illustrating four possible locations on a planting container at which an RFID tag may be deployed, according to various implementations.
Figure 4B:
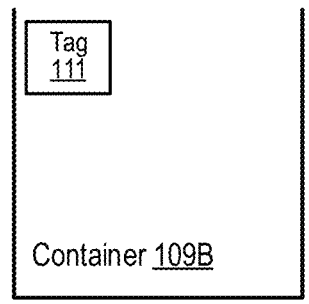
Figure 4C:
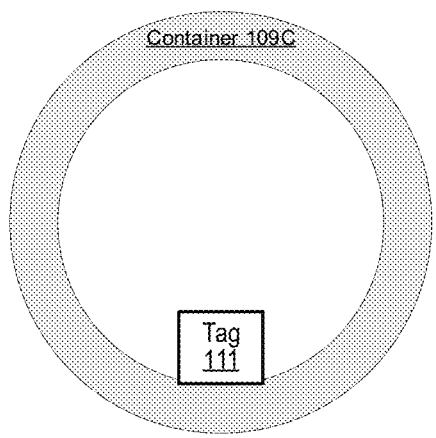
Figure 4D:
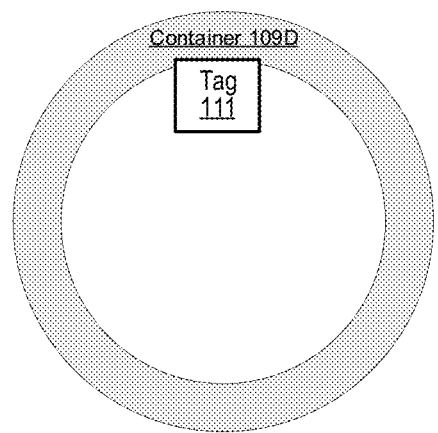

FIG. 3 illustrates the modules of an RFID soil moisture measuring manager 105, according to some implementations. As described above, the functionalities of the RFID soil moisture measuring manager 105 can reside on a single computer systems 210 such as the computing device 103 illustrated in FIG. 1, or be distributed between multiple computer systems 210, including within a cloud-based computing environment in which the functionality of the RFID soil moisture measuring manager 105 is provided as a service over a network 113 such as the internet. It is to be understood that although the RFID soil moisture measuring manager 105 is illustrated in FIG. 3 as a single entity, the illustrated RFID soil moisture measuring manager 105 represents a collection of functionalities, which can be instantiated as a single or multiple modules as desired (an instantiation of specific, multiple modules of the RFID soil moisture measuring manager 105 is illustrated in FIG. 3). It is to be understood that the modules of the RFID soil moisture measuring manager 105 can be instantiated (for example as object code or executable images) within the system memory 217 (e.g., RAM, ROM, flash memory) of any computer system 210, such that when the processor 214 of the computer system 210 processes a module, the computer system 210 executes the associated functionality. As used herein, the terms "computer system," "computer," "server," "server computer," "endpoint," "endpoint computer," "client," "client computer," and "computing device" mean one or more physical or virtual computers configured and/or programmed to execute the described functionality. Additionally, program code to implement the functionalities of the RFID soil moisture measuring manager 105 can be stored on computer-readable storage media. Any form of tangible computer readable storage medium can be used in this context, such as magnetic, optical or solid state storage media. As used herein, the term "computer readable storage medium" does not mean an electrical signal separate from an underlying physical medium.

The RFID functionality of the RFID soil moisture measuring system 101 is instantiated with an active reader-passive tag system, which consists of two parts: an active reader 107 and passive tags 111. The active reader 107 transmits interrogator signals to and receives authentication replies from passive tags 111. A passive tag 111 has no battery, thus it requires a reader 107 to transmit a high-power RF signal to active it, i.e., the passive tag 111 harvests energy from the reader's signal to power itself up. Then, the tag 111 replies to the reader 107 by reflecting the high power signal using ON-OFF keying modulation. Specifically, reflecting the reader's signal represents a '1' bit; otherwise it is a '0' bit. The active reader 107 transmitting a signal to the passive tag 111 can be described as interrogating the tag. Besides the tag's ID information, commodity RFID readers 107 provide us three signal features: Minimum Response Threshold ("MRT"), Received Signal Strength ("RSS"), and phase. These three parameters are now discussed.

A wireless signal S is typically represented as a complex number with amplitude $|S|$ and phase $\theta$, i.e., $S=|S|\cdot e^{j\theta}$. Suppose that $S_{TX}=|S_{TX}|\cdot e^{j\theta_{TX}}$ is the reader's transmission signal. Then, the signal received by a tag can be expressed as $$S_{Tag}=S_{TX}\cdot h_{Air}\cdot h_{Tag}, \qquad (1)$$

where $h_{Air}=|h_{Air}|\cdot e^{j\theta_{Air}}$ and $h_{Tag}=|h_{Tag}|\cdot e^{j\theta_{Tag}}$ are channel parameters over the air and the tag's antenna, and are complex numbers. Note that, in order to active a tag, the power of the tag's receiving signal $S_{Tag}$ must be higher than a threshold, i.e., the receiving sensitivity of a tag's chip. Suppose the receiving sensitivity of the tag is $P_{rx\text{-}sen}=20 \log|S_{Tag}^{min}|$, where $|S_{Tag}^{min}|$ is the weakest tag's receiving signal that can active the tag. Then, the required minimum transmission power, i.e., the MRT, of a reader to activate the tag is:

$$\text{MRT}=20 \log|S_{Tag}^{min}|-20 \log|h_{Air}|-20 \log|h_{Tag}|, \qquad (2)$$

where, $20 \log|h_{Air}|$ (<0) and $20 \log|h_{Tag}|$ (<0) are the one-way power loss over the air and the tag's antenna.

When a tag receives a reader's signal, it reflects the received signal for communication. The reflection is controlled by the tag's chip, and the reflection coefficient $\Gamma=|\Gamma|\cdot e^{j\theta_\Gamma}$, which is a constant for a given RFID chip. Then, the tag's reflection signal received by the reader can be expressed as:

$$\begin{aligned}S_{RX} &= S_{Tag}\cdot\Gamma\cdot h_{Tag}\cdot h_{Air} \\ &= S_{TX}\cdot\Gamma\cdot h_{Air}^2\cdot h_{Tag}^2 \\ &= \left|S_{TX}\Gamma h_{Air}^2 h_{Tag}^2\right|e^{j(\theta_{TX}+\theta_\Gamma+2\theta_{Air}+2\theta_{Tag})}.\end{aligned} \qquad (3)$$

The RSS and phase measured at the reader side are:

$$\text{RSS}=20 \log|S_{RX}|=20 \log|S_{TX}|+20 \log|\Gamma|+40 \log|h_{Air}|+40 \log|h_{Tag}|, \qquad (4)$$

$$\text{Phase}=\theta_{TX}+\theta_\Gamma+2\theta_{Air}+2\theta_{Tag}. \qquad (5)$$

where $20 \log|S_{TX}|(>0)$ is the transmission power of an RFID reader, $20 \log|\Gamma|(<0)$ is the reflection power loss $40 \log|h_{Air}|(<0)$ and $40 \log|h_{Tag}|(<0)$ are the round trip power loss over the air and the tag's antenna.

To summarize, the MRT, RSS, and phase features of an RFID tag 111 are related only to the channel parameters over the air and the tag's antenna, i.e., $h_{Air}$ and $h_{Tag}$ because other parameters in equations (2)-(5) are constants, e.g., the receiving sensitivity $P_{sen}$ of a tag, the reflection coefficient $\Gamma$ of a given RFID chip, and the reader's transmission signal $S_{TX}$ of a given reader setup.

In conjunction with FIGS. 1 and 3, the implementation and operation of the RFID soil moisture measuring system 101 is discussed according to some example scenarios. First, RFID signals are modelled in more detail to explain the signal changes caused by the soil moisture. Then, example implementations of components of the RFID soil moisture measuring system 101 are discussed, including signal feature selection, tag 111 type selection, and tag 111 deployment location selection. A robust system that is resilient to changes in the RF environment and pot locations is disclosed. Calibration of the RFID soil moisture measuring system 101 according to some example scenarios is also discussed below.

The physical principles that enable the RFID soil moisture measuring system 101 to estimate soil moisture levels from RFID signals are now described. More specifically, it is described herein how the MRT, RSS, and phase features of an RFID tag 111 are related only to the channel parameters over the air and the tag's antenna, i.e., $h_{Air}$ and $h_{Tag}$. For the sake of ease of illustration and understanding, equations (2), (4) and (5) are rewritten as follows:

$$\text{MRT}=C_1-20 \log|h_{Air}|-20 \log|h_{Tag}|, \qquad (6)$$

$$\text{RSS}=C_2+40 \log|h_{Air}|+40 \log|h_{Tag}|, \qquad (7)$$

$$\text{Phase}=C_3+2\theta_{Air}+2\theta_{Tag}, \qquad (8)$$

where $C_1$, $C_2$ and $C_3$ are constants. $C_1$ is the receiving sensitivity of a tag. $C_2$ and $C_3$ are related to the amplitude and phase of both the reader's transmission signal and the reflection coefficient of the tag's chip. As described below, these equations can be used to show why the moisture level of the soil in a container 109 to which an RFID tag 111 is affixed can change the associated MRT, RSS, and phase readings.

When an RFID tag 111 is attached to a pot containing soil, there is a coupling effect between the tag's antenna and the soil, since the tag 111 is physically proximate to the soil. This coupling happens even if the RFID tag 111 is not in direct contact with the soil. The coupling changes the electromagnetic field of the tag's antenna, resulting in changes to the channel $h_{Tag}$ over the tag's antenna. The amount of coupling is affected by the soil moisture level. Thus, when soil moisture varies, the channel $h_{Tag}$ over a tag's antenna will also change, causing changes to the MRT, RSS, and phase readings at the RFID reader 107.

Experiment confirms that soil moisture levels affects MRT, RSS, and phase readings. All three feature values vary when the soil moisture changes. MRT increases when the soil moisture increases, because the water inside the soil absorbs the signal received by the tag. The greater the amount of water added to the soil, the greater the signal attenuation over the tag's antenna, and thus a reader 107 needs to transmit more power (i.e., a large MRT) to activate the tag. Similarly, the RSS decreases as the soil moisture increases. The phase also changes over different soil moisture, since the soil moisture changes the channel $h_{Tag}$ over a tag's antenna.

Which signal feature(s) to use for sensing soil moisture in practice is now discussed. Although phase is affected by the level of soil moisture, phase does not change linearly when soil moisture changes. Hence, two different soil moisture levels may share the same phase value. Thus, phase is not an appropriate signal feature to use for soil moisture sensing. MRT and RSS are now discussed.

Based on Equations (6) and (7), note that MRT is related to the one-way channel between reader 107 and tag 111, but RSS is related to the round trip channel. Thus, intuitively, MRT should be less sensitive to environmental variations than RSS. More precisely, suppose that there is a channel change $\Delta h_{Air}$ over the air due to a change in the RF environment. Assuming that the soil moisture level does not change over this short time period, $h_{Tag}$ is a constant. Then, MRT variation $\Delta$MRT and RSS variation $\Delta$RSS can be expressed as:

$$\Delta MRT = 20\log|h_{Air} + \Delta h_{Air}| - 20\log|h_{Air}| \quad (9)$$
$$= 20\log\left|1 + \frac{\Delta h_{Air}}{h_{Air}}\right|,$$
$$\Delta RSS = 40\log|h_{Air} + \Delta h_{Air}| - 40\log|h_{Air}| \quad (10)$$
$$= 40\log\left|1 + \frac{\Delta h_{Air}}{h_{Air}}\right|.$$

Based on Equations. (9) and (10), we see that $$\Delta MRT = \frac{\Delta RSS}{2},$$

i.e., the variation of MRT is only the half of the RSS's variation. Note that it is half in dB, thus the amplitude variation of MRT would be the square root of the amplitude variation of RSS. This implies that, when there are changes in the RF environment, MRT is more robust than RSS.

When RF noise and additional reflection paths for the RFID signal are introduced (e.g., from people moving around, as would be common in a commercial greenhouse), variations occur in both MRT and RSS readings. As theory would suggest, experiment confirms that MRT has a much smaller variation compared with RSS in a dynamic RF environment. Thus, MRT is more robust for soil moisture sensing in a dynamic RF environment. As such, MRT is used as the signal feature for measuring soil moisture in some implementations of the RFID soil moisture measuring system 101 as described in more detail below.

In such implementations, a monitoring module 301 of the RFID soil moisture measuring manager 105 uses the relevant signal information gleaned from the reader 109 to monitor the MRT of the RFID tags 111 affixed to the various planting containers 109, based on the reader's wireless interrogation of the specific tags 111. A moisture level determining module 303 of the RFID soil moisture measuring manager 105 then determines soil moisture levels of the specific containers 109 based on monitored MRT and the known effects of soilure moisture on electromagnetic fields of antennas of passive RFID tags 111, as described in more detail below. It is to be understood that although less robust in dynamic RF environments, RSS may also be used for soil moisture sensing, and may be used in this context in other implementations of the RFID soil moisture measuring system 101. In those implementation, it is the RSS that is monitored and used to determine moisture levels.

Selecting a desirable type of passive RFID tag 111 for soil moisture sensing is now discussed. Different types of tags 111 vary in antenna structure and chip type, and consequently have different working ranges, sizes, and prices. It is desirable to use a passive RFID tag 111 type that has a relatively long working range so that the RFID reader 107 can read the tag 111 at a practicable distance even when the soil moisture level is high, because signal attenuation is used to sense moisture level. The higher the soil moisture level, the greater the attenuation in RFID signal, resulting in a reduced working range.

In an experiment with an RFID reader's transmission power set to maximum, the maximum working range was measured for tags of types A, B, C, D, E, and F attached to containers 109 with soil moisture levels of 6%, 48% and 92%. For each soil moisture level, each tag's working range was measured over 10 different deployment angles, making sure that the tag is still within the antenna's beamwidth. Type-E and Type-F tags 111 were experimentally determined to achieve working ranges of more than seven meters when the soil moisture is 6% (dry soil), and more than one meter even when the soil is moisture level is 92% (very wet soil). Type-E tags 111 are smaller than Type-F tags 111, allowing more convenient measurement of soil moisture level even in smaller containers 109. Moreover, Type-E tags 111 cost about six times less than Type-F tags 111. Thus, in one implementation, Type-E tags 111 are used, such as low cost Avery Dennison AD-383u7 tags. However, other types of off-the-shelf (commodity) passive RFID tags 111 are also feasible for soil moisture sensing, and in other implementations Type-F tags 111 are used, or other types such as, e.g., Type-B or Type-C.

There are different locations on or in a container 109 at which RFID tags 111 can be deployed. The effects of positioning RFID tags 111 at these different locations on sensing soil moisture are now discussed. FIG. 4A-D illustrate four possible locations on a container 109 at which an RFID tag 111 may be deployed: the outside of the container 109 above the soil level (4A), the outside of the container 109 below the soil level (4B), the inside of the container 109 above the soil level (4C), and the inside of the container 109 below the soil level (4D).

First discussed is the effects of placement of the tag 111 above or below the soil level, without regard to whether the tag is placed inside or outside of the container 109. When a tag 111 is deployed above the soil level, the MRT (or RSS) should not be affected by changes in the moisture levels, because the soil surface is below the tag and hence the extent of the coupling is not sufficient for the soil moisture to affect the signals features. This has been confirmed to be true experimentally. When a tag 111 is deployed below the soil level, the MRT increases when the moisture of the soil increases (or when more soil is added to the pot). Thus, in implementations of the RFID soil moisture measuring system 101 in which one tag 111 is deployed per container 109, the tag 111 is typically placed below the soil level (e.g., towards the bottom of the vertical surface of the container 109). Note that it is typically not practicable to deploy a tag 111 on the horizontal bottom surface of a container 109, because plants in greenhouses are typically watered from the horizontal bottom, through the use of watering trays.

Placement inside of the container 109 versus outside is now discussed for tags 111 deployed below the soil level. It has been experimentally determined that for tags 111 deployed on the inside of the container 109, the tag 111 stops responding to the reader 107 when the soil moisture level reaches about 80%, because the tag's antenna is in direct contact with the water. In contrast, when the tag 111 is deployed on the outside of the container 109, the tag 111 does not stop responding until the soil moisture level reaches 100%. Thus, in a presently preferred implementation of the RFID soil moisture measuring system 101, the tags 111 are deployed on the outside of the containers 109, although in other implementations tags 111 can be deployed on the insides.

Ideally, it would be desirable for the signal feature reading (e.g., MRT) to be related only to the soil moisture level. However, changes in the RF environment or changes in the locations of containers 109 (and hence, their associated tags 111) may cause variations in the channel $h_{Air}$ (in Equation (6)) over the air, which results in noisy MRT readings, and may cause errors in soil moisture level sensing. The impact of environmental variations and movement of containers 109 (and hence tags 111) on the RFID soil moisture measuring system 101 are now described.

Experiment confirms that MRT variations in a static RF environment are de minimums, whereas a dynamic RF environment (e.g., a scenario in which people are in motion such as in a commercial greenhouse) generally introduces noise into the MRT (or RSS) readings. If not addressed in the RFID soil moisture measuring system 101, these noisy MRT readings may cause errors in the corresponding determination of soil moisture levels. To remove variations caused by environmental changes, the RFID soil moisture measuring system 101 leverages the fact that changes in the soil moisture level are typically much slower than changes in the RF environment. In other words, moisture is depleted from soil much more slowly than people move about in greenhouses. Thus, in one implementation the moisture level determining module 303 applies a low pass filter to raw MRT values to remove environmental variations. Specifically, let $\{x_1, \ldots x_i \ldots x_N\}$ be a set of raw MRT readings. Then, the filtered MRT $y_i$ may be given by:

$$y_i = \alpha \cdot x_i + (1-\alpha) \cdot y_{i-1}, 2 \le i \le N, \tag{11}$$

where $y_1 = x_1$ and $\alpha$ = a smoothing factor. As $\alpha$ decreases, the output samples respond more slowly to a change in the input samples, i.e., the system is less sensitive to environmental changes. It is to be understood that the specific smoothing factor to use can vary between implementations as desired, as can the exact form of the low pass filter utilized. Experimentally, use of the low pass described above where $\alpha$ is 0.2 has been shown to remove most of the environmental noise in MRT, and is thus utilized in some implementations of the RFID soil moisture measuring system 101.

Figure 5:
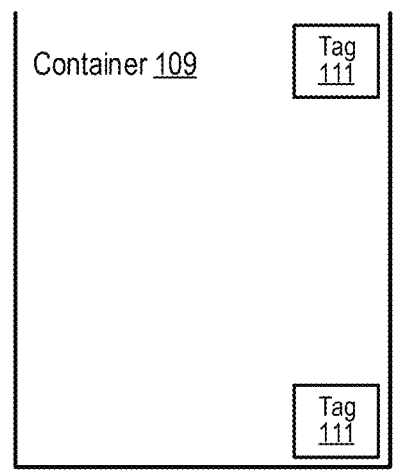
FIG. 5 illustrates an example implementation in which a sensing RFID tag and a reference RFID tag are affixed to a single planting container.

Typically, the locations of planting containers 109 are fixed in a greenhouse, in which case filtered MRT readings are related only to soil moisture levels. However, in some cases pots may be moved, such as when plants need more space as they grow. The changes in the locations of the containers 109 to which tags 111 are affixed can cause variations in MRT (or RSS) readings, which may result in soil moisture detection errors if not addressed. In one implementation, to address MRT variations caused by changes to container 109 (and hence tag 111) location, the moisture level determining module 303 uses a differential sensing method now described. More specifically, in this implementation, two tags 111 are co-deployed per each container 109, as illustrated in FIG. 5. A first tag $111_{FIRST}$ is deployed toward the bottom of the container 109 close to the soil, and a second tag $111_{SECOND}$ is deployed towards the top of the container 109 above the level of the soil. In this scenario, MRT readings of the first tag $111_{FIRST}$ deployed below the soil level are a function of both the soil moisture and the container's location, whereas MRT readings of the second tag $111_{SECOND}$ deployed above the soil level are only related to the location of the container 109. This is so because the coupling between the tag 111 and soil is only sufficient to affect the MRT for the first tag $111_{FIRST}$ deployed below the soil level, not for the second tag $111_{SECOND}$ deployed above the soil level. Because the two tags 111 are co-located at the same container 109, they will suffer from almost the same MRT variations caused by location changes. Thus, by calculating the differential MRT (DMRT) of the two tags 111, variations caused by location changes can be cancelled out and DMRT is only related to the soil moisture, not the container location. In this scenario, the first $111_{FIRST}$ deployed below the soil level functions as a sensing tag, whereas the second tag $111_{SECOND}$ deployed above the soil level functions as a reference tag.

It is to be understood that in practice in commercial greenhouses planting containers 109 are often filled with soil, so there is no surface area on the outside of the container 109 to which to attach the reference tag 111. In this scenario, the reference tag 111 can be affixed to the container 109 to attaching it to a label of the container, for example a plastic or wooden slat inserted in and protruding above the soil (or attached to the inside or outside of the pot) and used for labeling the plant growing in the container 109. In other implementations, a dedicated apparatus projecting above the soil level can be attached to the outside or inside of the container 109 or inserted in the soil, and used to affix the reference tag 111 above the soil level.

In order to map DMRT readings to specific soil moisture levels (i.e. 0% to 100%), the RFID tags 111 can be calibrated for soil moisture levels between 0% and 100%. To achieve this, the reader 107 may be positioned such that the maximum distance between the tags 111 and the reader's antenna is smaller than working range of the tag 111 at the highest moisture level to be measured. It is to be understood that the working range varies based on the type of passive RFID tags 111 and power of the specific reader 107 utilized.

Using a reader 107 positioned at a suitable distance from the tags 111 affixed to the containers 109, the monitoring module 301 measures DMRT values $[x_1, \ldots, x_i, \ldots, x_J]$ at given discrete soil moisture levels $[M_1, \ldots, M_i, \ldots, M_J]$ (ranging from 0% to 100%). The RFID soil moisture measuring manager 105 determines coefficients to use for a polynomial equation $M_i = p_1 x_i^n + p_2 x_i^{n-1} + \ldots + p_n x_i + p_{n+1}$ that maps the signal feature values $[x_1, \ldots, x_i, \ldots, x_J]$ to the specific discrete soil moisture levels $[M_1, \ldots, M_i, \ldots, M_J]$. Using this polynomial equation, the moisture level determining module 303 can then determine corresponding moisture level for any DMRT value. It is to be understood that the above described calibration can be done just once and then used for all containers 109 (and hence affixed tags 111) in the greenhouse. It is to be understood that in other implementations the RFID soil moisture measuring system 101 can be calibrated to measure soil moisture levels within a range other than 0%-100% as desired.

Figure 6:
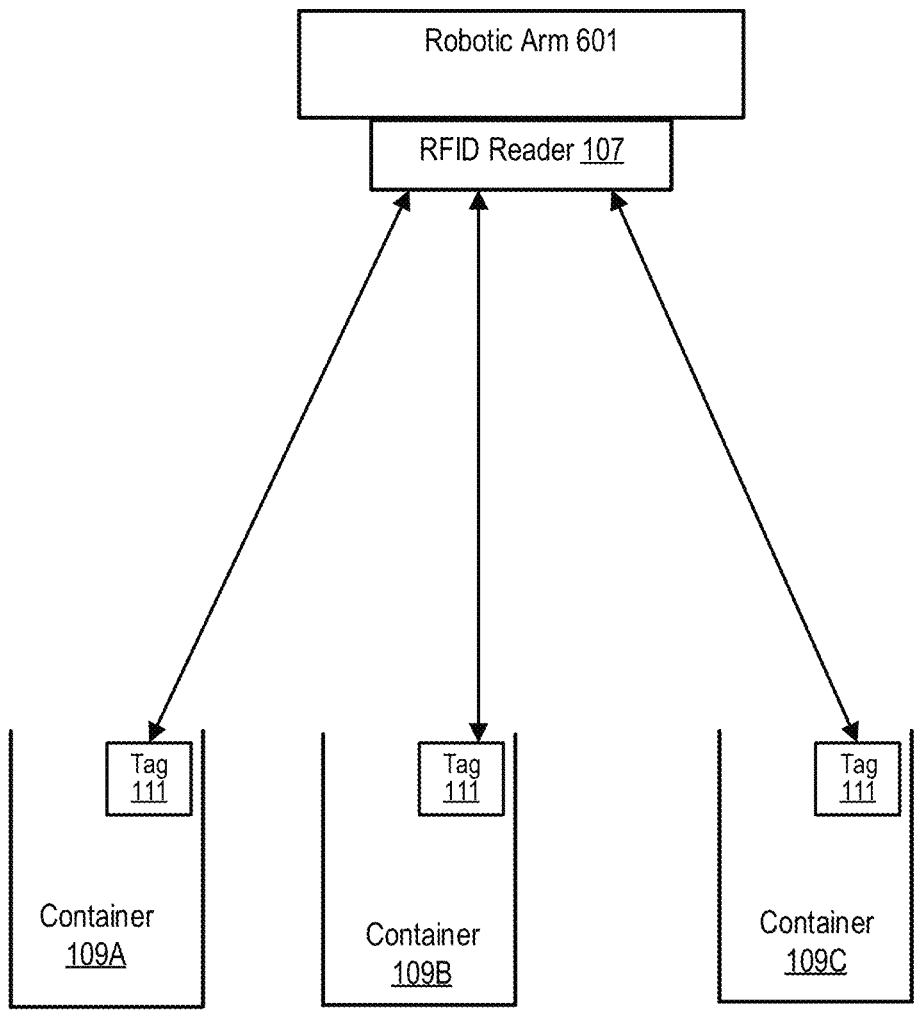
FIG. 6 illustrates an example implementation in which an RFID reader is affixed to a robotic arm.

As illustrated in FIG. 6, some greenhouses are equipped with a 3D movable robotic arm 601 for, e.g., spraying pesticides on plants. In some implementations the reader 107 is attached to the robotic arm 601, and the robotic arm is configured to pass over the containers within the working range of the tags 111 at maximum soil moisture level. For example, when using RFID tags with a working range of 1.2 meters at maximum soil moisture, the reader 107 can be attached to a robotic arm that the antenna is in less than 1.2 meters away from the lowest positioned tags 111 affixed to the containers 109. The reader 107 can then interrogate the tags as the robotic arm 601 moves above rows and/or columns of containers 109 in the greenhouse. In some implementations, multiple robotic arms 601 and/or readers 107 may be utilized.

Figure 7:
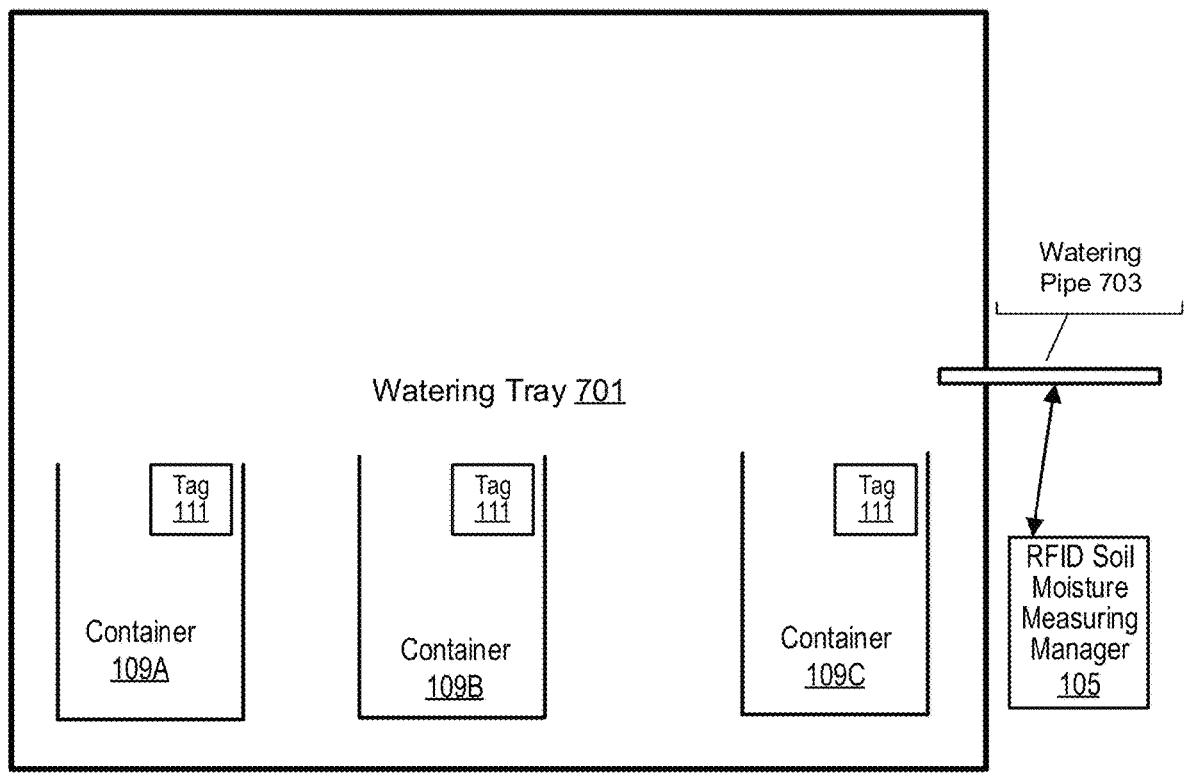
FIG. 7 illustrates an example implementation in which an RFID soil moisture measuring manager is configured for automatically irrigating planting containers.

As illustrated in FIG. 7, the containers 109 in the greenhouse may be placed on one or more watering trays 701, which may in turn be automatically irrigated by running water through one or more watering pipes 703, such that the soil in the containers takes up water from the trays 701 through openings in the container bottoms. In some implementations, in response to determining that soil moisture levels in one or more given containers 109 are below a given threshold (e.g., 5%, 15%, 25%, etc.), an irrigating module 305 of the RFID soil moisture measuring manager 105 automatically turns on or increases the flow of water through one or more watering pipe 703, to irrigate containers 109 positioned on a given watering tray 701.

As will be understood by those familiar with the art, the subject matter described herein may be embodied in other specific forms without departing from the spirit or integral characteristics thereof. Likewise, the particular naming and division of the portions, modules, agents, managers, components, functions, procedures, actions, layers, features, attributes, methodologies, data structures and other aspects are not mandatory or significant, and the entities used that implement the subject matter described herein may have different names, divisions and/or formats. The foregoing description, for purpose of explanation, has been described with reference to specific implementations. However, the illustrative discussions above are not intended to be exhaustive or limiting to the precise forms disclosed. Many modifications and variations are possible in view of the above teachings. The implementations were chosen and described in order to best explain relevant principles and their practical applications, to thereby enable others skilled in the art to best utilize various implementations with or without various modifications as may be suited to the particular use contemplated.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic device, that manipulates and transforms data represented as physical (electronic) quantities within the computer system's registers and memories into other data similarly represented as physical quantities within the computer system memories or registers or other such information storage, transmission or display devices.

Finally, the structure, algorithms, and/or interfaces presented herein are not inherently tied to any particular computer or other apparatus. Various general-purpose systems may be used with programs in accordance with the teachings herein, or it may prove convenient to construct more specialized apparatus to perform the method blocks. The structure for a variety of these systems will appear from the description above. In addition, the specification is not described with reference to any particular programming language. It will be appreciated that a variety of programming languages may be used to implement the teachings of the specification as described herein.

Accordingly, the disclosure is intended to be illustrative, but not limiting, of the scope of the subject matter set forth in the following claims.

What is claimed:

1. A computer-implemented method for measuring levels of soil moisture in a plurality of containers using passive Radio Frequency Identification ("RFID") tags, wherein each one of the plurality of containers contains soil, the method comprising:
   automatically wirelessly interrogating, by at least one RFID reader, specific passive RFID tags affixed to or inside of specific ones of the plurality of containers;
   automatically monitoring at least one signal feature of the specific passive RFID tags affixed to or inside of the specific ones of the plurality of containers, based on the wireless interrogation of the specific passive RFID tags;
   wherein the least one signal feature of a passive RFID tag further comprises a minimum response threshold of RFID reader transmission power to activate the passive RFID tag ("MRT"); and
   automatically determining soil moisture levels of the specific ones of the plurality of containers based on the at least one monitored signal feature of the specific passive RFID tags, and effects of soilure moisture on electromagnetic fields of antennas of passive RFID tags.

2. The method of claim 1 further comprising:
   automatically detecting a change in a soil moisture level of a specific container based on a change in at least one signal feature of at least one specific associated passive RFID tag.

3. The method of claim 1 further comprising:
   applying a low pass filter to raw MRT readings $\{x_1, \ldots x_i \ldots x_N\}$ taken for a specific passive RFID tag, wherein a filtered MRT value $y_i$ is calculated as $y_i = \alpha \cdot x_i + (1-\alpha) \cdot y_{i-1}$, $2 \leq i \leq N$, where $y_1 = x_1$ and $\alpha = $ a given smoothing factor; and
   using filtered MRT values to automatically determine soil moisture levels.

4. The method of claim 1 wherein:
   two passive RFID tags are proximately positioned to a given container, a first passive RFID tag being positioned below a level of soil in the given container, and a second passive RFID tag being positioned above the level of soil.

5. The method of claim 4 wherein:
   the first passive RFID tag is affixed to the outside of the given container below the level of soil, and the second passive RFID tag is affixed to the outside of the given container above the level of soil.

6. The method of claim 4 further wherein the least one signal feature of a passive RFID tag further comprises an MRT, the method further comprising:
   calculating a differential MRT ("DMRT") of the first passive RFID tag positioned below the level of soil and the second passive RFID tag positioned above the level of soil, the DMRT comprising the difference between the MRT of the first tag and the MRT of the second tag; and
   automatically determining the soil moisture level of the given container based on the calculated DMRT.

7. The method of claim 1 wherein the least one signal feature of a passive RFID tag further comprises:
a received signal strength (RSS) of a reflection signal of the passive RFID tag.

8. The method of claim 1 wherein passive RFID tags further comprise:
Type-E passive RFID tags.

9. The method of claim 1 wherein passive RFID tags further comprise:
Type-F passive RFID tags.

10. The method of claim 1 wherein the at least one RFID reader is attached a movable robotic arm, the method further comprising:
the robotic arm automatically moving above multiple rows and columns of containers; and
the at least one RFID reader attached to the robotic arm automatically wirelessly interrogating passive RFID tags affixed to or inside of containers in the multiple rows and columns as the robotic arm moves.

11. The method of claim 1 further comprising:
automatically mapping features of signals to soil moisture levels by measuring signal feature values $[x_1, \ldots, x_i, \ldots, x_J]$ at specific discrete soil moisture levels $[M_1, \ldots, M_i, \ldots, M_J]$ ranging from 0% to 100%.

12. The method of claim 11 further comprising:
applying a polynomial equation $M_i = p_1 x_i^n + p_2 x_i^{n-1} + \ldots + p_n x_i + p_{n+1}$ mapping the signal feature values $[x_1, \ldots, x_i, \ldots, x_J]$ to the specific discrete soil moisture levels $[M_1, \ldots, M_i, \ldots, M_J]$ to determine a corresponding moisture level for a specific signal feature value.

13. The method of claim 1 further comprising:
responsive to determining that soil moisture levels are below a given threshold, automatically irrigating at least a subset of the plurality of containers.

14. A system for automatically measuring levels of soil moisture, the computerized system comprising:
a plurality of containers each containing soil;
at least one passive RFID tag affixed to or positioned inside of each specific container;
at least one RFID reader positioned above the plurality of containers, the at least one RFID reader being configured to wirelessly interrogate the passive RFID tags affixed to or positioned inside the containers;
at least one computing device communicatively coupled to the at least one RFID reader, the at least one RFID reader and the at least one computing device being configured to communicate using RFID reader protocol, and the at least one computing device comprising a memory and at least one processor;
a monitoring module residing in the memory, the monitoring module being configured to monitor at least one signal feature of the specific passive RFID tags affixed to or inside of the specific ones of the plurality of containers, based on the wireless interrogation of the specific passive RFID tags; and
a moisture level determining module residing in the memory, the moisture level determining module being configured to determine soil moisture levels of the specific ones of the plurality of containers based on the at least one monitored signal feature of the specific passive RFID tags wherein the least one signal feature of a passive RFID tag further comprises a minimum response threshold of RFID reader transmission power to activate the passive RFID tag ("MRT"), and effects of soilure moisture on electromagnetic fields of antennas of passive RFID tags.

15. The system of claim 14 wherein:
two passive RFID tags are proximately positioned to a given container, a first passive RFID tag positioned below a level of soil in the given container, and a second passive RFID tag positioned above the level of soil.

16. The system of claim 15 the system further comprising:
the moisture level determining module is further configured to calculate a DMRT of the first passive RFID tag positioned below the level of soil and the second passive RFID tag positioned above the level of soil, the DMRT comprising the difference between the MRT of the first tag and the MRT of the second tag; and
the moisture level determining module is further configured to determine the soil moisture level of the given container based on the calculated DMRT.

17. The system of claim 14 further comprising:
a movable robotic arm to which the at least one RFID reader is attached, the movable robotic arm being configured to move automatically over multiple rows and columns of containers; and wherein
the at least one RFID reader attached to the robotic arm is configured to wirelessly interrogate passive RFID tags affixed to or inside of containers in the multiple rows and columns as the robotic arm moves.

18. The system of claim 14 further comprising:
at least one watering tray on which the containers are positioned;
at least one watering pipe configured to add water to the at least one watering tray; and
an irrigating module residing in the system memory, the irrigation module being configured to automatically control the flow of water through at least one watering pipe to irrigate containers positioned on the at least one watering tray, responsive to the determining module determining that soil moisture levels are below a given threshold.

19. The system of claim 14 further wherein:
the containers further comprise pots containing soil and plants; and
the systems is physically located in a greenhouse.

* * * * *